United States Patent [19]

Marinov et al.

[11] Patent Number: 4,545,252

[45] Date of Patent: Oct. 8, 1985

[54] APPARATUS FOR THE DETERMINATION OF CONTACT STRESSES IN PRESTRESSED TIRED (SHRINK-FITTED) TOOLS

[75] Inventors: Mihail T. Marinov; Lyubomir T. Petkanchin; Georgi I. Pushev; Georgi T. Kostov; Mitko M. Mihovski; Valentina A. Manolova, all of Sofia, Bulgaria

[73] Assignee: Institute po Metaloznanie i Technologia na Metalite, Sofia, Bulgaria

[21] Appl. No.: 533,207

[22] Filed: Sep. 6, 1983

[30] Foreign Application Priority Data

Sep. 16, 1982 [BG] Bulgaria ................................. 57976

[51] Int. Cl.$^4$ ............................................ G01N 29/04
[52] U.S. Cl. ................................................. 73/633; 73/637
[58] Field of Search ............... 73/633, 635, 637, 638, 73/640, 582

[56] References Cited

U.S. PATENT DOCUMENTS

| | | |
|---|---|---|
| 3,266,300 | 8/1966 | Grabuski ................................. 73/637 |
| 3,289,468 | 12/1966 | van der Veer et al. ............... 73/637 |
| 3,531,982 | 10/1970 | Clotfelter et al. .................... 73/582 |
| 4,246,794 | 1/1981 | Sheets et al. ........................... 73/637 |
| 4,457,174 | 7/1984 | Bar-Cohen et al. .................. 73/582 |

*Primary Examiner*—Anthony V. Ciarlante

[57] ABSTRACT

The apparatus comprises a base and two movable opposite centers, one of which is fastened to a rotatable axle, while the other is fastened to a screw by means of a bearing, and mounted in two opposite parallel plates. Between the plates there is disposed a tank filled with an acoustic medium, and underneath it there is mounted a sensor which is connected to a measuring system. Two parallel guides are transversely fastened to the plates. The base is suspended on the parallel guides with a collar fastened to it. The base is provided with a driving screw and a handle. A spring, within the collar and attached to it, is fastened rigidly to a guiding sleeve. To this sleeve there is fastened the tank, on which there are seated parallel rotating rollers. A limiting sleeve of the sensor is mounted inside a guide by means of a locking nut, which is pressed against a second nut fastened to the guiding sleeve.

4 Claims, 2 Drawing Figures

APPARATUS FOR THE DETERMINATION OF CONTACT STRESSES IN PRESTRESSED TIRED (SHRINK-FITTED) TOOLS

BACKGROUND OF THE INVENTION

This invention relates to an apparatus for the determination of contact stresses in prestressed tired (shrink-fitted) tools intended for mechanical working by plastic deformation, and for the determination of contact stresses in shrink-fitted joints.

A known apparatus for the determination of contact stresses (Bulgarian patent specification No. 28,809) comprises two movable opposite centers, between which the inspected component is placed. One of these centers is fastened to a rotatable axle, while the other is fastened to a screw by means of a bearing. Both centers are mounted in opposite parallel plates. The plates are connected by means of a clamp. Between the plates, there is a tank supported by a base and containing an acoustic medium. Through the base and the bottom of the tank there is arranged an axially movable guide, in the hole of which there is an ultrasonic sensor, which is connected to a measuring system.

A drawback of the known apparatus lies in the necessity of manually maintaining a constant distance between the inspected component and the sensor in each measuring operation.

SUMMARY OF THE INVENTION

It is a general object of the invention to provide an apparatus for the automatic determination of contact stresses, thus eliminating errors due to subjective adjustments made during each measuring operation.

This object is achieved by an apparatus which comprises a base and two movable rotating opposite changeable centers, one of which is fastened to a rotatable axle, while the other is fastened to a screw by means of a bearing. Both centers are mounted, respectively, on two opposite parallel plates. Between the plates there is disposed a tank containing an acoustic medium, and to the bottom of the tank there is fastened an axially movable guide, in the bore of which there is mounted a sensor, which is connected to a measuring system. Two parallel guides are fastened transversely to the parallel plates, and the base is suspended on the guides. A collar is movably mounted in and fastened to the base by means of a leading screw and a nut. The base is provided with a driving screw and a handle. A spring, within the collar and attached to it, is fastened rigidly to a guiding sleeve, part of which is embraced by the collar. Between the guiding sleeve and the collar there is a radial clearance. To the guiding sleeve there is fastened the tank, on which there are seated parallel rotating rollers inside the tank. The axially movable guide is connected to a limiting sleeve of the sensor inside it by means of a locking nut, which is pressed against a second nut fastened to the guiding sleeve.

The advantages of the apparatus according to the invention lie in the possibility of automating the process of determining the contact stresses and the non-destructive testing of prestressed tired (shrink-fitted) tools, as well as for rapid detection of any deviations in the interference of the shrink-fit of the tool.

BRIEF DESCRIPTION OF THE DRAWING

The invention will be more readily understood with reference to the accompanying schematic drawings showing a preferred embodiment thereof.

DETAILED DESCRIPTION OF THE DRAWING

Figure 1:
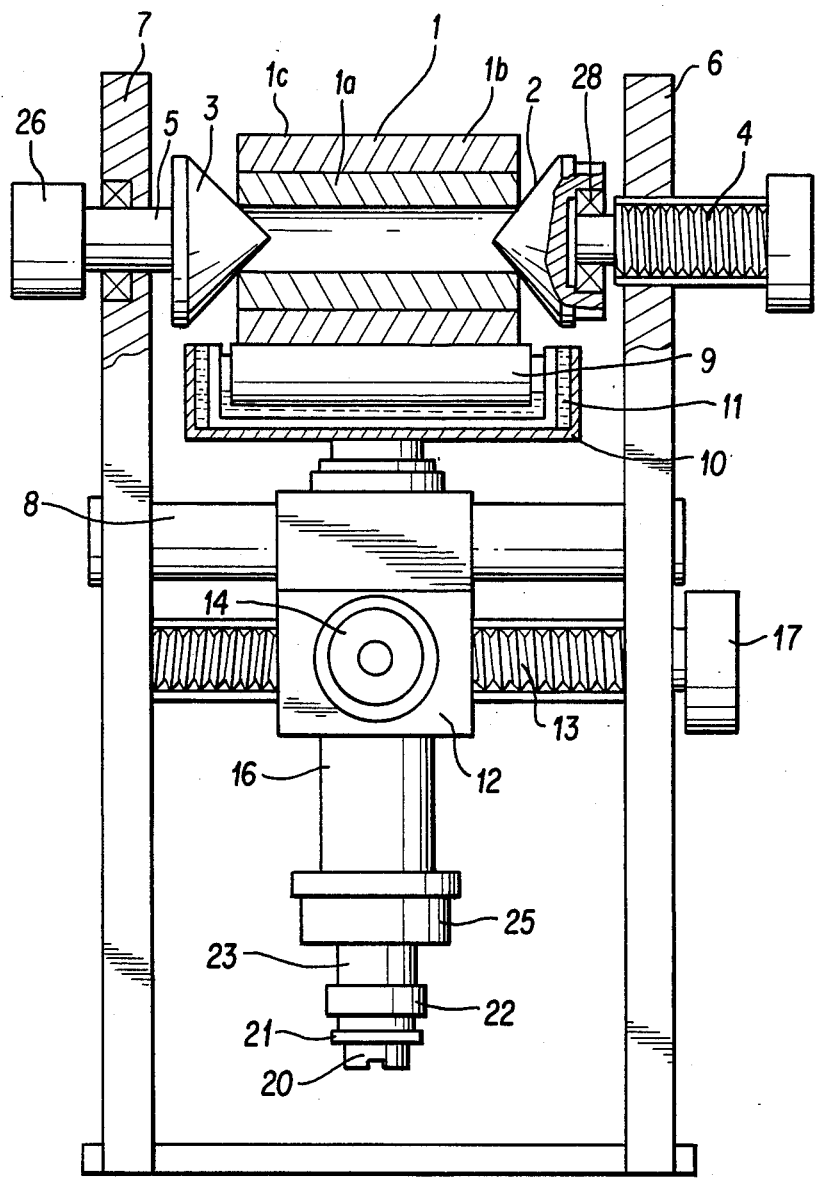
FIG. 1 is a general elevational view partialy in cross-section of the apparatus of this invention.
Figure 2:
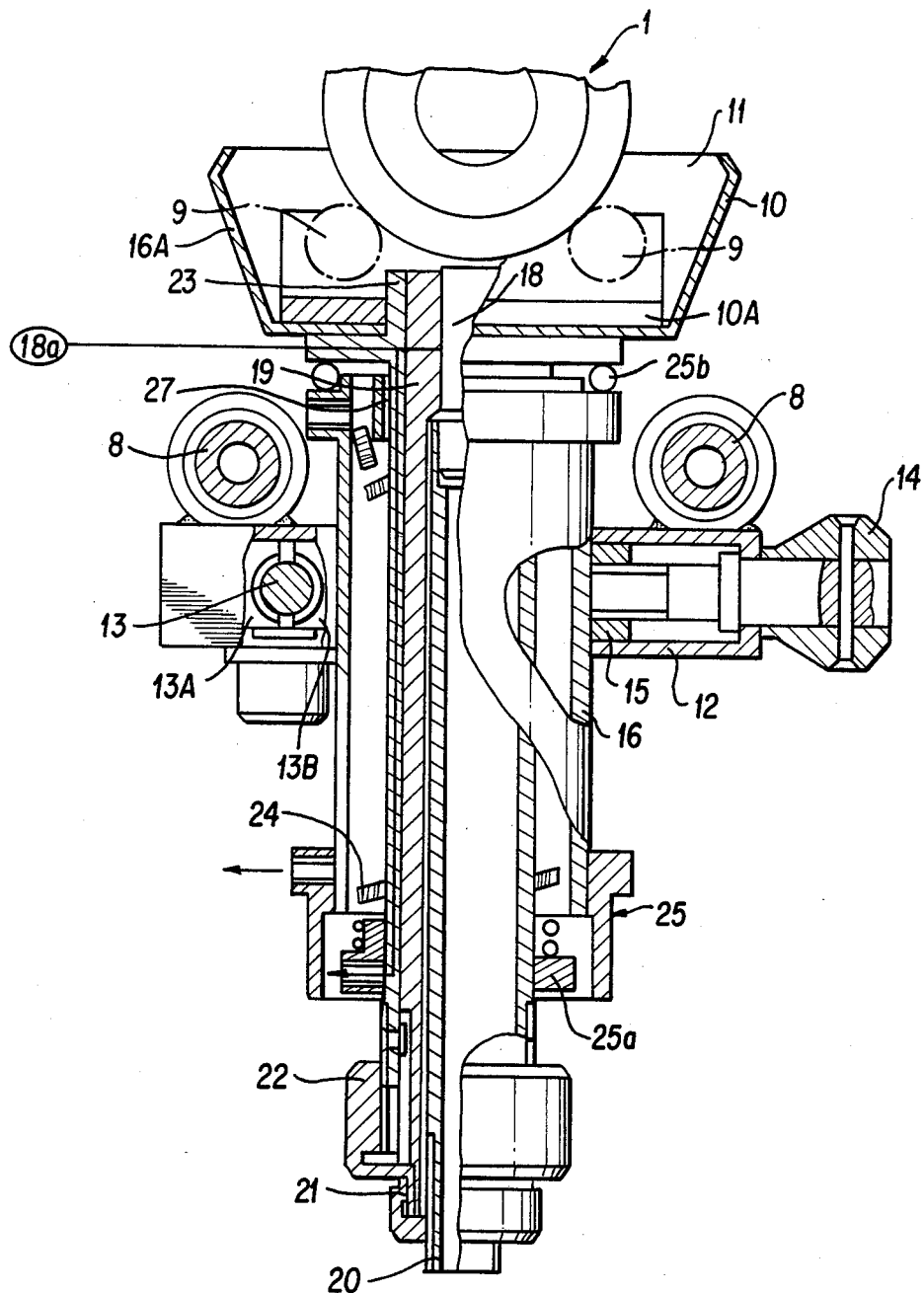
FIG. 2 illustrates partially in cross-section the floating system of the apparatus of the invention.

The inspected prestressed tool 1 is fixed between two opposite changeable rotating centers 2 and 3, which are fastened, respectively, to a screw 4 by means of a bearing 28 and to a rotatable axle 5 with handle 26. The centers are mounted, respectively, to the parallel plates 6 and 7, which in turn are connected by means of parallel guides 8. (FIG. 1). The tool 1 is in contact with the parallel rotating rollers 9, via a guiding sleeve 23, a spring 24, and a collar 16 with radial clearance 27 mounted on movable base 12. The rollers 9 are fixedly mounted on guiding sleeve 23 and are seated in the tank 10. This tank is filled with an acoustic medium 11. Base 12 is suspended from the parallel guides 8 and is connected with a driving screw 13 by a cut through nut 13a and 13b. (FIG. 2) Collar 16 is fastened within base 12 by means of a leading screw 14 and a nut 15.

A unit is mounted within collar 16 comprising rollers 9 within body 10a; the adjacent tank 10 containing acoustic medium 11; guiding sleeve 23 to which tank 10 is rigidly connected; and sensor 18 fixed in the bore of the axially movable guide 19 by limiting sleeve 20 and nuts 21 and 22. The components of the unit are suspended within the collar by 16 by spring 24, which is fastened rigidly at its bottom end to the guiding sleeve 23 by ring 25a. Guiding sleeve 23 has a radial clearance 27 with respect to collar 16.

MANNER OF OPERATION

The operation of the apparatus is as follows. The inspected prestressed tool 1 is fixed between the centers 2 and 3 and is tightened between them by means of a screw 4.

The coarse adjustment of the sensor 18 with respect to the tool 1 is effected by moving the collar 16, with its suspended unit of elements in a vertical direction by means of the sleeve 25, until the upper ring 25b touches the flange of sleeve 23 and a desired compression force is produced between the rollers 9. The tool 1, and the collar 16 is then fixed in position by adjusting the leading screw 14 and the nut 15.

The fine adjustment of the sensor 18 with respect to the contour of the tool 1 is effected by rotating the second nut 22 thereby threadably adjusting the guide 19 relative to the guide sleeve 23. The radial clearance 27 and spring 24 allows a self-adjustment of the rollers 9 to the contour of the tool 1, because the tank 10 and rollers 9 self-adjust their position via a relative movement between the collar 16, on the one hand, and the guide 19 and guide sleeve 23, on the other hand. The loading nut 21 acts to keep limiting sleeve 20 and sensor 18 in a constant position with respect to guides 19 and support motion of guide 19, when driven by nuts 22.

The effective position of the sensor 18 on the surface of the tool 1 is achieved by displacing the base 12 together with the collar 16 and the unit attached to it, by means of the handle 17 and the rotation of the tool 1 by means of a second handle 26. For each position, the sensor 18 emits signals which are excited by a source (not shown in the drawing), and records the signals reflected from the boundary surface 1c between the die 1a and the tire 1b by means of a recording device (not shown in the drawing). The excitation and the recording can be effected by means of an ultrasonic flaw detector.

Although the invention is described and illustrated with reference to a single embodiment thereof, it is to be expressly understood that it is in no way limited to the disclosure of such preferred embodiment but is capable of numerous modifications within the scope of the appened claims.

We claim:

1. An apparatus for the determination of contact stresses in prestressed tired (shrink-fitted) tools, comprising:
    a base having two coaxial and opposingly rotatable mounted supports, one of which is fastened to a rotatable axle, while the other is fastened to a screw by means of a bearing, and which are respectively mounted in two opposite parallel plates;
    a tank containing an aromatic medium disposed between the plates;
    an axially-movable first guide sleeve fastened to the bottom of the tank; the guide sleeve having a first bore in which sensing means are operatively mounted; the sensing means being operatively connected to a measuring system;
    two parallel guides forming a connection between the parallel plates and on which the base is suspended;
    means within the parallel guides adapted to position the tank bidirectionally with respect to the tired tool;
    means within the axially-movable guide sleeve adapted to position the sensing means in a vertical direction with respect to the tank; and
    means within the tank adapted to maintain a contact distance between the tank and the surface of the tired tool.

2. An apparatus as described in claim 1 wherein the means for positioning the tank with respect to the tired tool comprises:
    a collar which coaxially embraces the guide sleeve and is adapted to be movably mounted jointly with the base on the pair of parallel guides;
    a leading screw and nut which adjusts the vertical position of the collar with respect to the base; and
    a driving screw which moves the base along the parallel guides.

3. An apparatus as described in claim 2 wherein the means for positioning the sensing means with respect to the tank comprises:
    a guide coaxially and movably mounted in said sleeve,;
    a second bore within the axially-movable guide sleeve, the sensing means being affixed therein by a limiting sleeve inserted within the bore; and
    a locking nut pressed against a second nut fastened to the guiding sleeve and connecting the limiting device to the axially-movable guide.

4. An apparatus as in claim 1 wherein the means for maintaining a constant distance between the tank and the surface of the tired tool comprises:
    a spring coaxially embracing the guide sleeve and being coaxially mounted in said collar and biasing said guide sleeve and the sensing means disposed therein against said tired tool; and
    a radial clearance between the collar and the guiding sleeve; and wherein
    the tank is mounted on the guiding sleeve; and
    the parallel rotating rollers are rotatably mounted inside the tank.

* * * * *